United States Patent [19]

Preikschat et al.

[11] Patent Number: 5,012,118

[45] Date of Patent: Apr. 30, 1991

[54] APPARATUS AND METHOD FOR PARTICLE ANALYSIS

[76] Inventors: Fritz K. Preikschat, 16020 Lake Hills Boulevard, Bellevue, Wash. 98008; Ekhard Preikschat, 9048 41st St., Bellevue, Wash. 98004

[21] Appl. No.: 450,603

[22] Filed: Dec. 13, 1989

[51] Int. Cl.[5] .......................................... G01N 15/06
[52] U.S. Cl. .................................... 250/574; 356/336
[58] Field of Search ............... 356/335, 336, 28, 28.5; 250/573, 574, 560

[56] References Cited

U.S. PATENT DOCUMENTS

| | | | |
|---|---|---|---|
| 3,532,427 | 10/1970 | Paine | 356/28 |
| 3,676,647 | 7/1972 | Staffin et al. | 235/92 PC |
| 3,858,851 | 1/1975 | Ogle | 356/102 |
| 3,941,477 | 3/1976 | Schodl | 356/28 |
| 3,998,552 | 12/1976 | Stewart et al. | 356/103 |
| 4,140,395 | 2/1979 | Kreikebaum | 356/336 |
| 4,387,993 | 6/1983 | Adrian | 356/336 |
| 4,492,467 | 1/1985 | Drain et al. | 356/336 |
| 4,537,507 | 8/1985 | Hess | 356/336 |
| 4,725,136 | 2/1988 | McCullough et al. | 356/28 |

FOREIGN PATENT DOCUMENTS

| | | |
|---|---|---|
| 035437 | 2/1981 | European Pat. Off. . |
| 289677 | 11/1988 | European Pat. Off. . |
| 1919628 | 4/1971 | Fed. Rep. of Germany . |
| 3315456 | 12/1984 | Fed. Rep. of Germany . |
| 1305923 | 3/1970 | United Kingdom . |

OTHER PUBLICATIONS

"Analysis of Suspended Solids by Single-Particle Scattering", S. R. Diehl, D. T. Smith, and M. Sydor. Applied Optics, vol. 18, No. 10, May 15, 1979, p. 1653.
"Heterogeneous Nucleation and Droplet Growth", O Preining, P. E. Wagner, F. G. Pohl, and W. Szymanski. Part III of Aerosol Research at the Institute for Experimental Physics of the University of Vienna, Feb. 1981.

Primary Examiner—David C. Nelms
Attorney, Agent, or Firm—Christensen, O'Connor, Johnson & Kindness

[57] ABSTRACT

Apparatus and method of analyzing particles contained in a fluent medium. An optical system receives light from a laser, and focuses the light at a focal spot in the fluent medium. Optical pulses resulting from the backscattering of light by particles in the focal spot are detected and used to produce an electrical transit time signal comprising a series of electrical pulses. The length of each electrical pulse corresponds to the time required for a particle to pass through the focal spot. The apparatus also includes a laser Doppler system that receives light from the focal spot region, and produces an electrical velocity signal corresponding to the velocity of particles within such region. A processor receives the transit time and velocity signals, and combines the signals to produce data representing the sizes of particles passing through the focal spot.

14 Claims, 3 Drawing Sheets

APPARATUS AND METHOD FOR PARTICLE ANALYSIS

FIELD OF THE INVENTION

The present invention relates to an apparatus and method for analyzing the sizes of particles in a fluent medium.

BACKGROUND OF THE INVENTION

There exist many applications in industry and science in which it is required to determine the number of particles suspended in a fluent (i.e., liquid or gaseous) medium, and the sizes or size distribution of such particles. Such measurements can be very important in manufacturing processes in a number of industries, including pharmaceuticals, plastics, chemicals, and paper. Processes such as crystal growth, precipitation, polymerization, gravimetric separation and grinding must be monitored with regard to the sizes of suspended particles, to control the quality of the final product. Ideally, particle measurements should be made on-line, to provide real time information for process control, and to avoid distorting particle size information by removing samples from the process.

In the past, a number of different technologies have been developed for the analysis of particle size. One prior optical technique, described in U. S. Pat. No. 4,871,251, utilizes a focused light beam from a laser diode source. Using this technique, one is able to obtain a very small sensing volume at a focal spot in the fluent medium, and therefore a very high light intensity at the focal spot. This intensity is high enough to overcome the natural falloff in the intensity of light scattered into backward angles. This makes individual light pulses, coming from individual particles going through the focal spot, detectable by ordinary detection means. This prior technique also includes scanning the focused light beam at a near-constant speed, such that by measuring the pulse length of each of the light pulses, one can determine particle size. One can implement mechanical scanning mechanisms relatively easily for scanning rates up to about 3 meters per second.

The technology described above can in principle be used for airborne particles. Such particles are encountered in dry milling and grinding applications, and in applications requiring the measuring of the size of vapor droplets such as those coming out of injector nozzles in fuel injection systems or in spray nozzles used in the fertilizer industry. In practice, however, the typical flow velocities for airborne particles are much higher than the scanning rates readily obtainable from mechanical scanning mechanisms. For example, in fluidized flows, powders are air-conveyed at velocities as high as 30 meters per second. In order to make an optical particle measurement system insensitive to flow velocity, the laser beam would have to be scanned at a velocity much higher than the material flow. While one can design higher speed electronic detection circuits, it is generally not feasible to implement mechanical scanning means that can achieve the required scanning rates.

One possible solution for measuring airborne particles would be to introduce baffles into the material flow, in an attempt to slow down the flow rate. It has been found, however, that this approach leads to agglomeration effects, causing particles to stick together, therefore producing an erroneous reading. In practice, it has been found to be very difficult to get a well dispersed dry powder sample. Another possible approach would be to use off-line measurements. However such measurements are cumbersome, time-consuming, and cannot be done in real time.

As a result of these consideration, there is a strong, presently unmet need for an effective means for measuring particle size for airborne powders and the like. Some attempts have been made to make measurements at very low material concentrations, where the laser beam can pass through the material, and where only a few particles are illuminated at any one time. In such a case, one can use the traditional Frauenhofer diffraction measurements. This method, however, fails at the higher material concentrations that are typically encountered in most applications.

SUMMARY OF THE INVENTION

The present invention provides an apparatus and method for analyzing particles contained in a fluent medium. The invention is capable of handling the high flow rates typically found in airborne particle suspensions. The invention provides an on-line technique that does not require baffles, and that does not require the medium to flow through a sample chamber.

In a preferred embodiment, an apparatus according to the present invention comprises illumination means that includes a laser, and an optical system for receiving light from the laser and focusing the light at a focal spot in the fluent medium. Optical pulses resulting from the backscattering of light by particles in the focal spot are detected to produce an electrical transit time signal comprising a series of electrical pulses. The length of each electrical pulse corresponds to the time required for a particle to pass through the focal spot. The apparatus also includes a laser Doppler system that receives light from a region that includes the focal spot, and produces an electrical velocity signal corresponding to the velocity of particles within such region. A processor receives the transit time and velocity signals, and combines such signals to produce data representing the sizes of particles passing through the focal spot.

DETAILED DESCRIPTION OF THE INVENTION

Figure 1:
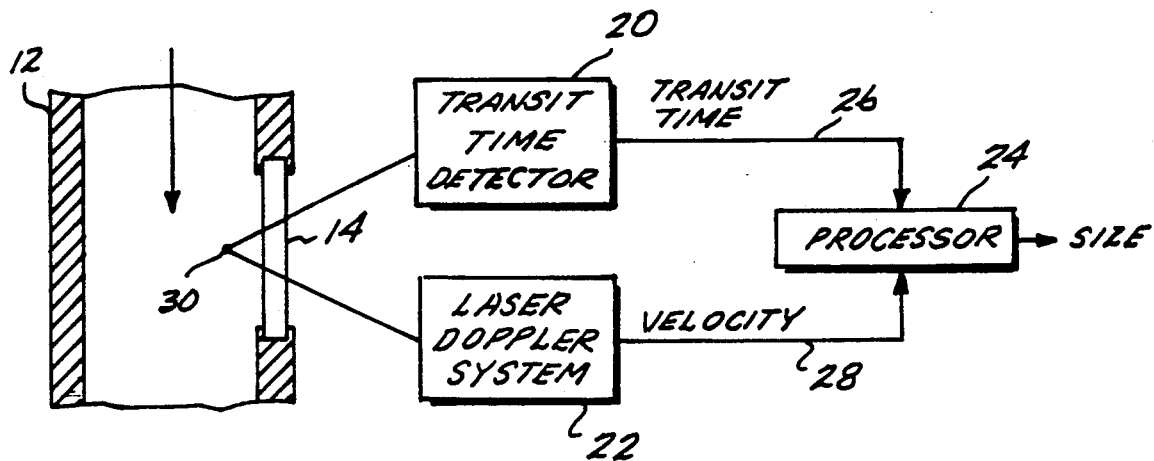
FIG. 1 is a schematic diagram of the particle analysis system of the present invention.
Figure 2:
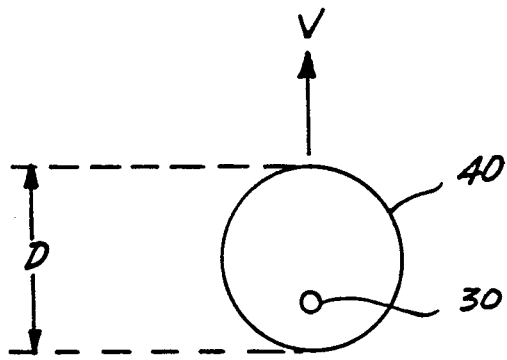
FIG. 2 illustrates the relationship between the focal spot and a particle passed through the focal spot.

The particle analysis technique utilized in the present invention is illustrated in schematic form in FIGS. 1 and 2. In FIG. 1, it is assumed that a suspension of solid or liquid particles is flowing through conduit 12 in th direction indicated by the arrow. Conduit 12 includes window 14, through which light can pass. The apparatus used in the present invention to analyze the particles in conduit 12 includes transit time detector 20, laser Doppler system 22, and processor 24. Transit time detector 20 produces a light beam that passes through window 14, and that is focused at focal spot 30 in the fluent medium. Particles going through focal spot 30 produce brief pulses of light that are detected by the transit time detector. The transit time detector converts the light pulses into corresponding electical pulses, to produce a transit time signal on line 26. The time duration of each electrical pulse is equal to the time duration of the corresponding optical pulse. Each pulse on line 26 therefore represents the time that a given particle was in focal spot 30.

Laser Doppler system 22 includes means for detecting light reflected from focal spot 30 or the vicinity thereof. The reflected light can either be the light produced by transit time detector 20, or the laser Doppler system can include its own illumination means. By analyzing the frequency of the reflected light, the laser Doppler system produces a signal on line 28 that indicates the velocity of flow at the focal spot.

The time signal on line 26 and the velocity signal on line 28 are received by processor 24, and converted by the processor into a measurement of particle size. Referring to FIG. 2, it is assumed that particle 40 having a diameter D and moving with a velocity V is passing through focal spot 30. It can readily be seen that the time required for particle 40 to pass through focal spot 30 will be equal to D/V. The length of the pulse on line 26 will therefore be equal to D/V, and processor 24 can determine the diameter D by simply multipying velocity by time (pulse length) to obtain the particle diameter. Processor 24 can of course implement more complex models that may be required for nonspherical particles, or for particles having diameters approaching that of focal spot 30.

Figure 3:
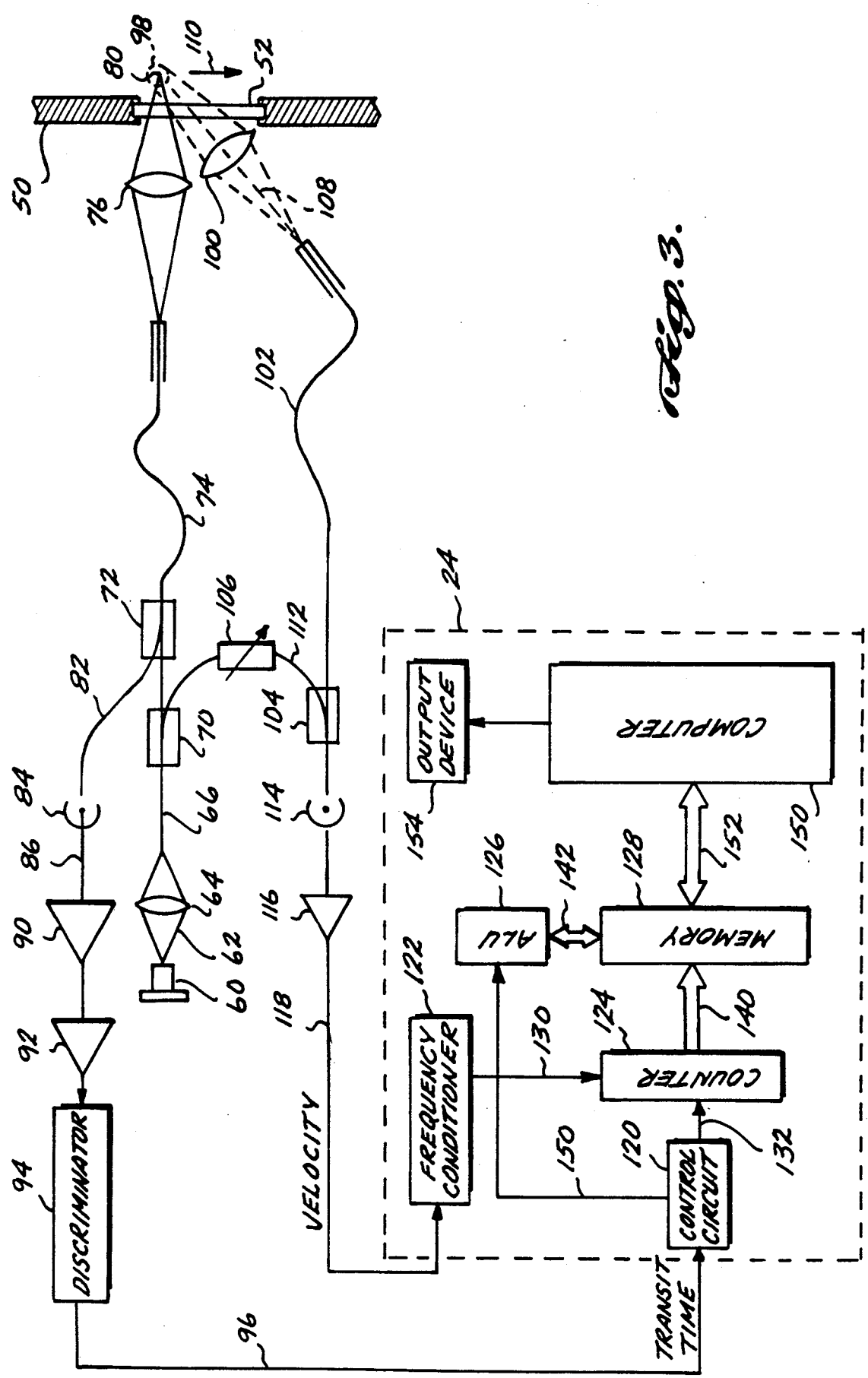
FIG. 3 is a block diagram of a preferred embodiment of the system.

A preferred embodiment of the particle analysis system of the present invention is shown in greater detail in FIG. 3. The particles to be analyzed are assumed to be flowing within a conduit, partially shown at 50, in which a window 52 is formed. The transit time detector includes a laser diode 60 (upper left portion of FIG. 3) that produces a beam 62 that is focused by lens 64 into fiber-optic cable 66. A laser diode with a pigtail output connector could also be used. The light on fiber-optic cable 66 passes through directional couplers 70 and 72, into fiber-optic cable 74. Light emerging from the tip of fiber-optic cable 74 is focused by lens 76 to spot 80 within the fluent medium.

Pulses of light reflected by particles at focal spot 80 are picked up by lens 76, focused into fiber-optic cable 74, and the return pulses are then coupled by directional coupler 72 into fiber-optic cable 82 that terminates at photodetector 84. The photodetector therefore produces a signal on line 86 that comprises a series of pulses, each pulse having a pulse length corresponding to the transit time of a particle through focal spot 80.

The signal on line 86 is first amplified by preamplifier 90, and then passes through logarithmic amplifer 92 that reduces the dynamic range of the signal amplitude, to permit a wider range of materials to be measured. The output of logarithmic amplifier 92 is then input to discrimination circuit 94. Discrimination circuit 94 passes only those pulses having rise times below a certain threshold, as described in greater detail in U.S. Pat. No. 4,871,251, hereby expressly incorporated by reference. As described in that patent, discrimination circuit 94 prevents the counting of particles that do not pass directly through focal spot 80. The output of discrimination circuit 94 on line 96 comprises the transit time signal that is input to processor 24.

In the preferred embodiment shown in FIG. 3, the laser Doppler system comprises lens 100, fiber-optic cable 102, directional coupler 104, and variable attenuator 106. The illumination utilized by the laser Doppler system is the light provided by laser diode 60 via lens 76. In particular, when light is focused to a small focal spot in a fluent medium in which particles are suspended, a halo 98 of light is created around the focal spot. The halo 98 is produced by multiple scattering, by light that is scattered by particles before the light reaches the focal spot, or by the scattering of light that passes through the focal spot.

Lens 100 has an optical axis 108. Lens 100 is positioned so as to collect light reflected from halo 98, and focus such light into fiber-optic cable 102. The frequency of such light will be Doppler shifted due to the movement of the particles within halo 98. In particular, the light reflected from halo 98 will have a frequency f given by $$f = (c' + v \cos \alpha)/\lambda \text{tm} \quad (1)$$

where $c'$ is the velocity of light within the fluent medium, v is the flow velocity of the fluent medium and the particles embedded therein, $\lambda$ is the wavelength of the light, and $\alpha$ is the angle between optical axis 108 and flow direction 110.

Light from halo 98 that is collected by lens 100 is focused into fiber-optic cable 102. This light is combined in directional coupler 104 with a local oscillator signal on fiber-optic cable 112. The local oscillator signal is derived from the light produced by laser diode 60 via coupler 70. The intensity of the local oscillator signal is controlled by variable attenuator 106, so that it approximately matches the intensity of the Doppler shifted signal on fiber-optic cable 102. These two signals are mixed in photodetector 114, and the resulting electrical signal is amplified by preamplifier 116, to produce the velocity signal on line 118 that is input to processor 24.

Processor 24 includes control circuit 120, frequency conditioner 122, counter 124, ALU (adder) 126, and memory 128. The velocity signal on line 118 is input to frequency conditioner 122. The frequency conditioner preferably comprises a low-pass filter for extracting the Doppler frequency component from the velocity signal on line 118. Optionally, frequency conditioner 122 also comprises a frequency divider or a frequency multiplier, for altering the Doppler frequency in a manner consistent with the desired accuracy of the system. The frequency conditioner produces a conditioned velocity signal on line 130 that is coupled to the clock input terminal of counter 124.

The transit time signal on line 96 is input to control circuit 120. As described above, the transit time signal comprises a series of pulses, each pulse having a duration corresponding to the size of a particle that has passed through the focal spot. Control circuit 120 passes such pulses directly to the count enable input terminal of counter 124 via line 132. As a result, counter 124 counts the cycles of the conditioned velocity signal on line 130, for a period of time governed by the length of each pulse on line 132. Thus in effect, counter 124 multiplies the length of each pulse by the frequency of the conditioned velocity signal. As a result, the count accumulated by counter 124, at the end of each pulse, is proportional to the diameter of the particle that gave rise to the pulse.

Memory 128 contains a memory location for each of the possible counts accumulated by counter 124. Thus if counter 124 is an 8-bit counter, memory 128 contains 256 memory locations. The count accumulated by counter 124 at the end of each transit time pulse is output on bus 140, and the accumulated count forms the address input for memory 128. Also at the end of each transit time pulse, control circuit 120 provides an enable signal on line 150 that is received by ALU 126. In response, ALU 126 adds one to the number stored in the addressed location in memory 128. Thus at the end of a predetermined counting interval, each location in memory 128 contains a number equal to the number of particles detected by the system in a given size range.

Processor 24 further includes computer 150 that is coupled to memory 128 via bus 152, and output device 154. After each counting interval, computer 150 reads the data stored in memory 128, and resets the memory values to zero in preparation for the next counting interval. Computer 150 can then process the size data read from memory 128 in a suitable manner, and output such data via output device 154.

In an alternate embodiment, each individual count accumulated by counter 124 would be stored in a separate location in memory 128, and computer 150 would process such data by determining the total number of counts for each count value. In such an embodiment, the accumulated counts on bus 140 are input to the data input terminals of memory 128, and ALU 126 would be replaced by a memory control circuit that provided a suitable address signal on bus 142. However, in general, the illustrated embodiment is preferred, because it requires fewer memory locations.

Figure 4:
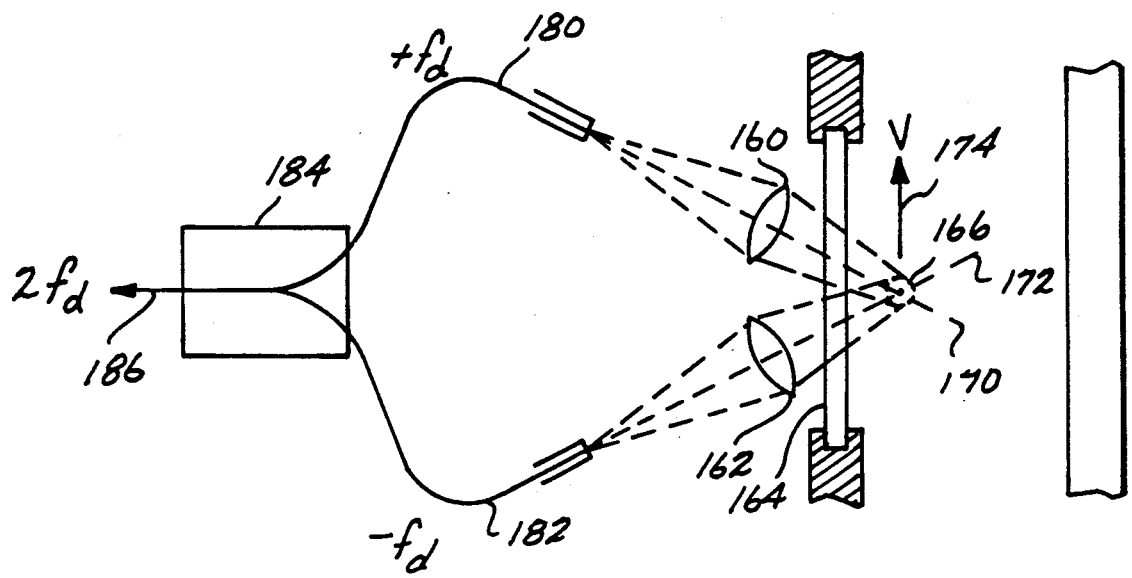
FIG. 4 is an optical schematic diagram of a second preferred embodiment of the laser Doppler system.

A second preferred embodiment of the laser Doppler system is illustrated in FIG. 4. The illustrated system includes lenses 160 and 162 that are positioned adjacent window 164, and that are adapted to collect and focus light from halo 166 in the fluent medium. Lens 160 has an optical axis 170 oriented at an angle $\alpha$ with respect to flow direction 174, while lens 162 has an optical axis 172 that also forms an angle $\alpha$ with the flow direction. Light collected by lens 160 is focused into fiber-optic cable 180, while light collected by lens 162 is focused into fiber-optic cable 182.

With the direction 174 as shown in FIG. 4, the signal on fiber-optic cable 180 will include a positive Doppler shift $f_d$ of magnitude $v\cos\alpha/\lambda$, while light on fiber-optic cable 182 will include a negative Doppler shift $-f_d$ of equal magnitude. The signals on fiber-optic cables 180 and 182 are combined in optical coupler 184, resulting in an output optical signal on fiber-optic cable 186 that includes a difference frequency $2f_d$ at twice the Doppler shift frequency. This signal can be utilized in a manner similar to that shown in FIG. 3 to produce the velocity signal.

Figure 5:
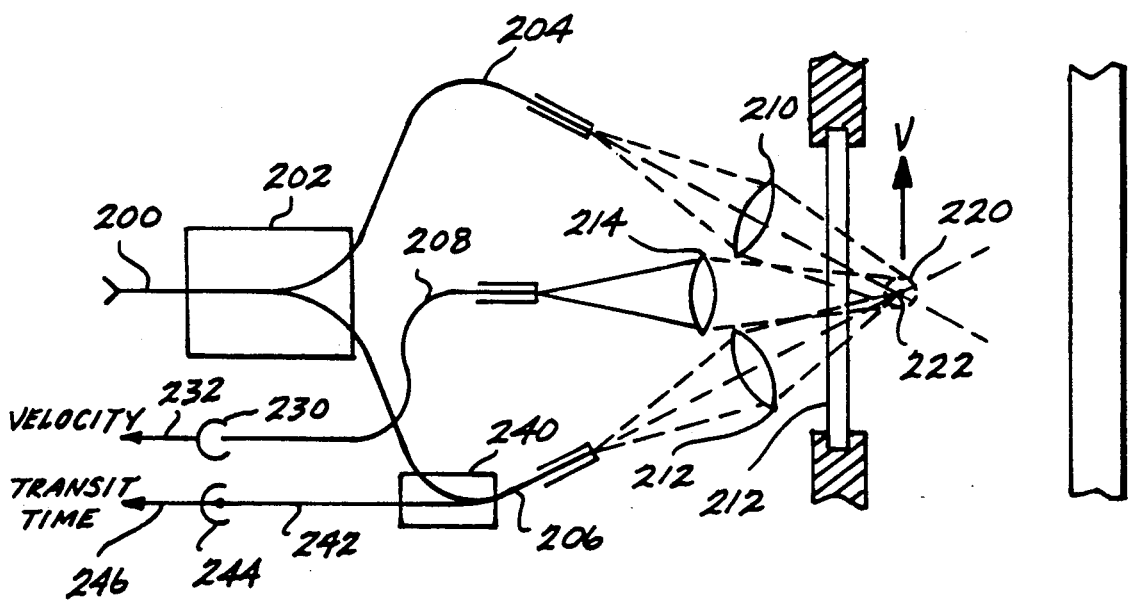
FIG. 5 is a block diagram of a third preferred embodiment of the invention.

A third preferred embodiment of the invention is illustrated in FIG. 5. In this arrangement, laser light on fiber-optic cable 200 is input to optical coupler 202, to produce a pair of optical signals on fiber-optic cables 204 and 206, respectively. Lens 210 focuses the light from fiber-optic cable 204 onto halo region 220 in the fluent medium, while lens 212 focuses the light from fiber-optic cable 206 at a small focal spot 222 within halo region 220. Lens 214 collects light from within halo region 220, and focuses the light into fiber-optic cable 208.

In this embodiment, light from fiber-optic cables 204 and 206 forms an interference pattern within halo 220. A particle traversing the halo therefore passes through such interference pattern, and produces an alternating optical signal that is picked up by lens 214. The frequency of such signal is proportional to particle velocity, as in the embodiment shown in FIGS. 3 and 4. This signal is converted by photodetector 230 to produce the velocity signal on line 232. The bright single pulse of light resulting from the passage of the particle through focal spot 222 is picked up by lens 212, to produce a corresponding optical signal on fiber-optic cable 206. This signal is coupled by coupler 240 into fiber-optic cable 242, and the resulting optical signal is converted by photodetector 244 into a transit time signal on line 246. The transit time signal may then be subjected to logarithmic amplification and rise time discrimination, as in the embodiment shown in FIG. 3. The difference between this embodiment and that of FIGS. 3 and 4 is that in this embodiment, the optical interference takes place at the focal spot, rather than in an optical coupler.

While the preferred embodiments of the invention have been illustrated and described, variations will be apparent to those skilled in the art. Accordingly, the scope of the invention is to be determined by reference to the following claims.

The embodiments of the invention in which an exclusive property or privilege is claimed are defined as follows:

1. An apparatus for analyzing particles contained in a fluent medium, the apparatus comprising:
   illumination means comprising a laser and an optical system for receiving light from the laser and focusing the light at a focal spot in the fluent medium;
   detection means for detecting optical pulses resulting from the backscattering of light by particles in the focal spot, and for producing an electrical transit time signal that comprises a series of electrical pulses, the length of each electrical pulse corresponding to the time required for a particle to pass through the focal spot;
   a receiver system for receiving light from a region that includes the focal spot, and for producing an electrical velocity signal corresponding to the velocity of particles within said region; and
   processing means for receiving the transit time and velocity signals, and for combining the transit time and velocity signals to produce data representing the sizes of particles passing through the focal spot.

2. The apparatus of claim 1, wherein the velocity signal has a frequency corresponding to the velocity of particles within said region.

3. The apparatus of claim 1, wherein the processing means includes means for providing a clock signal having a frequency proportional to the velocity of particles within said region, and means for counting cycles of the clock signal for a period of time proportional to the length of each electrical pulse.

4. The apparatus of claim 1, wherein the light received by the receiver system principally comprises light originating in the laser.

5. The apparatus of claim 4, wherein the receiver system comprises beam-splitting means for receiving light from the laser and producing a local oscillator signal, means for receiving light from the region that includes the focal spot to produce an optical sensor signal, and means for combining the local oscillator and sensor signal and converting the combined signal into the velocity signal.

6. The apparatus of claim 1, wherein the receiver system comprises means for receiving light from said region from first and second directions and producing corresponding first and second optical signals, and means for combining the first and second optical signals to produce a third optical signal that includes a beat component at a frequency proportional to the velocity of the particles within the region.

7. The apparatus of claim 1, wherein the detection means comprises a photodetector for converting the optical pulses into a corresponding electrical detection signal, and a logarithmic amplifier for amplifying the detection signal to produce the transit time signal.

8. The apparatus of claim 1, wherein the optical system comprises means for dividing light from the laser to produce first and second optical illumination signals, means for focusing the first illumination signal at the focal spot, and means for focusing the second illumination signal into a volume in the fluent medium that includes the focal spot.

9. A method for analyzing particles contained in a fluent medium, the method comprising:
producing laser light and focusing the laser light at a focal spot in the fluent medium;
detecting optical pulses resulting from the backscattering of light by particles in the focal spot, and producing an electrical transit time signal comprising a series of electrical pulses, the length of each electrical pulse corresponding to the time required for a particle to pass through the focal spot;
receiving light from a region that includes the focal spot, and producing an electrical velocity signal having a frequency corresponding to the velocity of particles within said region; and
combining the transit time and velocity signals to produce data representing the sizes of particles passing through the focal spot.

10. The method of claim 9, wherein the velocity signal has a frequency corresponding to the velocity of particles within said region.

11. The method of claim 9, wherein the combining step comprises providing a clock signal having a frequency proportional to the velocity of particles within said region, and counting cycles of the clock signal for a period of time proportional to the length of each electrical pulse.

12. The method of claim 9, wherein the step of producing the electrical velocity signal comprises producing a local oscillator signal from the laser light, and combining the local oscillator signal with the light received from said region to produce the velocity signal.

13. The method of claim 9, wherein the receiving step comprises receiving light from said region from first and second directions and producing corresponding first and second optical signals, and wherein the means for producing the electrical velocity signal comprises means for combining the first and second optical signals to produce a third optical signal that includes a beat component at a frequency proportional to the velocity of the particles within the region, and converting the third optical signal into the electrical velocity signal.

14. The method of claim 9, wherein the step of producing laser light comprises dividing light from a laser to produce first and second illumination beams, focusing the first illumination beam at the focal spot, and focusing the second illumination beam into a volume in the fluent medium that includes the focal spot.

* * * * *